United States Patent [19]
Raghoenath et al.

[11] Patent Number: 6,150,143
[45] Date of Patent: *Nov. 21, 2000

[54] NATAMYCIN RECOVERY

[75] Inventors: Dilipkoemar Raghoenath, Rotterdam; Josephus J. P. Webbers, Maassluis, both of Netherlands

[73] Assignee: Gist-Brocades B.V., Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/797,503

[22] Filed: Feb. 7, 1997

Related U.S. Application Data

[60] Provisional application No. 60/011,367, Feb. 9, 1996.

[51] Int. Cl.[7] ....................................................... C12P 17/11
[52] U.S. Cl. ........................ 435/119; 435/253.5; 536/6.5
[58] Field of Search ................... 435/253.5, 119, 435/252.1; 424/93.43; 514/31; 536/6.5

[56] References Cited

U.S. PATENT DOCUMENTS

| | | | |
|---|---|---|---|
| 3,892,850 | 7/1975 | Struyk | 424/119 |
| 4,600,706 | 7/1986 | Carter | 514/31 |
| 4,690,894 | 9/1987 | Brierley | 435/244 |
| 4,950,477 | 8/1990 | Schmitt | 424/43 |
| 5,266,347 | 11/1993 | King | 426/623 |
| 5,591,438 | 1/1997 | Olson | 424/195.1 |
| 5,686,273 | 11/1997 | Eisenschink | 435/119 |
| 5,902,579 | 5/1999 | Eisenschink | 424/93.43 |

FOREIGN PATENT DOCUMENTS

| | | |
|---|---|---|
| 844289 | 3/1957 | United Kingdom . |
| WO 9507998 | 3/1995 | WIPO . |
| WO 9527073 | 10/1995 | WIPO . |

OTHER PUBLICATIONS

Crueger et al., "Biotechnology: a Textbook of Industrial Microbiology" 2nd. Ed., Sinauer Assoc., 1990.

*Primary Examiner*—Irene Marx
*Attorney, Agent, or Firm*—Bierman, Muserlian and Lucas

[57] ABSTRACT

A process for the recovery of natamycin from a fermentation broth containing biomass and natamycin, which comprises:
  (a) disintegrating the biomass; and
  (b) separating the natamycin from the thus treated fermentation broth.

5 Claims, No Drawings

NATAMYCIN RECOVERY

PRIOR APPLICATION

This application is based on provisional application Ser. No. 60/011,367 filed Feb. 9, 1996.

This invention relates to a process for recovering natamycin.

Natamycin, also known as pimaricin or tennecetin, is a polyene antibiotic which has been known since the late fifties (Struyk, et al, Antibiot. Ann. 1957–1958, 878).

For more than 20 years, natamycin has been used to prevent the growth of mould and yeast on cheese and sausages. More recent developments on the use of natamycin have been described in WO 93/00913 (Use of natamycin for the treatment and prevention of poultry mycosis), WO 93/01720 (Natamycin treatment of dried whole kernel grains), WO 93/00911 (Use of natamycin for the control and prevention of poultry Aspergillosis) and WO 93/00912 (Use of natamycin for the prevention and control of poultry Dactylarlosis).

Natamycin is prepared by fermentation processes such as those disclosed in GB-A-844289 using *Streptomyces natalensis*, or those disclosed in GB-A-846933, WO 93/03169, WO 93/03170 and WO 93/03171 using *Streptomyces gilvosporeus*.

After the natamycin has been produced, for example by the fermentation processes described above, the natamycin is recovered by extraction processes such as those described in GB-A-844289, GB-A-846933, WO 92/10580, WO 95/07998 or WO 95/27073. All these recovery processes require large amounts of organic solvent. More recently described recovery processes (e.g. those disclosed in WO 92/10580, WO 95/07998 and WO 95/27073) use a procedure wherein an organic solvent is added to the broth and the pH of the broth is adjusted to solubilize the natamycin. Thereafter the suspended solids are removed by filtration. Lastly the pH of the filtrate is re-adjusted to precipitate the natamycin and the precipitated natamycin is removed from the remaining liquid.

Both WO 92/10580 and WO 95/07998 use methanol as the organic solvent. The pH of the broth is adjusted to 1–4.5 to solubilize the natamycin, the broth is filtered and the natamycin is precipitated again by raising the pH to 6–9.

In WO 95/27073 isopropanol is used as the organic solvent. The isopropanol is added after the pH has been adjusted to 10–11, and subsequently the insoluble solids are removed by crossflow filtration and the natamycin is precipitated by adjustment of the pH to 5.5–7.5.

In the recovery processes described above there is a (partial) removal of water before the recovery procedure starts, in order to minimize the amount of organic solvent required. Drying and solid/liquid separation techniques are described to remove water. All of these recovery processes use organic solvents, which results in high recovery costs and in environmental drawbacks.

It has now been found that natamycin of high purity can be recovered from a fermentation broth using a recovery process which does not require the use of organic solvents.

The present invention provides a process for the recovery of natamycin from a fermentation broth containing biomass and natamycin which comprises:

(a) disintegrating the biomass; and (b) separating the natamycin from the thus treated fermentation broth.

Fermentations producing natamycin usually result in a fermentation broth comprising natamycin, biomass solids, dissolved or suspended nutrients, other fermentation products and water.

The fermentation broth in general contains at least 2 g/l natamycin, preferably at least 7 g/l natamycin. For example the natamycin concentration in the fermentation broth can be about 7 g/l as disclosed in WO 93/03170. Since natamycin has a very low solubility in water, the natamycin is mainly present in solid form in the fermentation broth. Solid natamycin means 'natamycin not dissolved in water'. The solid form of natamycin present in the fermentation broth may preferably comprise natamycin particles. Natamycin particles are natamycin crystals which, for example, may have the following forms: needle-formed crystals, disc-formed crystals or the like. During the fermentation natamycin particles are formed. The natamycin particles usually have diameters of from 0.5–20 micrometer. The diameter of the natamycin particle is the largest distance from one part of the particle to the other end of the particle. Needle-formed natamycin particles with diameters of more than 40 micrometer have been observed. Diameters may be determined using a microscope.

The biomass of the Streptomyces organisms used in the production of natamycin generally consists of clusters (mycelia) of threads, although other forms of biomass, e.g. the so-called "pellets", may be present as well. In these threads (hyphae) compartments are present, in which cellular activities are localized. The size of these threads as present in the clusters is in general from 10–30 micrometer (diameters ranging from 0.5–1.0 micrometer).

Up to now separation of the natamycin from the biomass and other impurities was not possible without using an organic solvent.

Surprisingly, we found that when the size of the particles of the biomass is reduced, the biomass can subsequently be efficiently separated from the natamycin particles in the aqueous phase.

Thus, in the present invention, after the fermentation, the fermentation broth is treated to disintegrate the biomass. Disintegration of the biomass may result in lysis, solubilization of cell matters, and fragmentation (size reduction) of the clusters and threads. Disintegration of the biomass may be checked by viewing the biomass with a microscope (magnification 400×). Disintegration is complete if hardly any clusters or threads of the biomass can be viewed with a microscope. Disintegration of the biomass can also be determined by measuring the viscosity of the fermentation broth. For example during the disintegration of a biomass of the cluster-type, the viscosity decreases. If the viscosity does not substantially decrease on further treatment, the biomass will be sufficiently disintegrated. Although different fermentation conditions or different Streptomyces organisms used in the production of natamycin may result in somewhat different forms of biomass present at the end of the fermentation, one skilled in the art is able to find a suitable duration for the disintegration of the biomass of any fermentation broth.

Homogenization, high shear mixing and ultrasonic techniques or heat-, pH- (alkaline), or enzymatic treatments or treatment with surface active agents can, for example, be used alone or in combination to disintegrate the biomass. The disintegration techniques are chosen in such a way that disintegration is obtained without substantially affecting the natamycin. Most of the natamycin, at least 80%, preferably up to 100%, keep their solid form and natamycin activity will not substantially reduce. Furthermore, it will be clear to one skilled in the art that the disintegration techniques may not substantially affect the natamycin particle size. If particle size of natamycin is reduced like the particle size of the biomass, then separation of the natamycin from the biomass would be difficult. An efficient example of disintegration is the use of a heat treatment optionally combined with a pH-treatment.

A heat treatment can be applied to the fermentation broth at the end of the fermentation (e.g. in the fermenter, after all supplies (e.g. oxygen, carbon or nitrogen sources) have ceased). The heat treatment may be carried out, for example, for 1 to 8 hours and, for example, at 30 to 50° C. Preferably the heat treatment may be carried out at 30 to 35° C. Higher temperatures may result in flocculation, precipitation and coagulation, which would adversely affect separation of the biomass from the natamycin particles.

A pH-treatment for, for example, 1 to 8 hours and, for example, at a pH of 8 to less than about 10 can also be easily conducted at the end of the fermentation in the fermenter. At pH's above 10 natamycin will become more soluble and more vulnerable to inactivation, which would adversely affect recovery yield and purity of the final natamycin. Sodium hydroxide or any other compatible caustic material, for example ammonium hydroxide or potassium hydroxide, can be used to increase the pH. After the alkaline incubation the broth is neutralized by hydrochloric acid or another compatible acid, for example phosphoric acid, sulphuric acid or acetic acid. Preferably neutralization takes place after separating the natamycin from the fermentation broth.

Enzymatic-treatments can involve the incubation with cell wall decomposing and/or organic polymer decomposing enzymes such as lysozym, xylanase, cellulase, protease, glucanase, lipase and amylase. The enzymes alone or as mixtures of enzymes, are generally incubated under the optimum conditions for the enzymes to operate. The enzymes contribute to the lysis of cells and to the solubilization of organic polymers.

Homogenization can involve the use of a Manton-Gaulin type homogenisator. The fermentation broth is forced through an orifice. Due to pressure forces the biomass will disintegrate.

Disintegration of the biomass by ultrasonic techniques can be obtained by applying ultrasonic waves to the fermentation broth, that will provide for oscillation of cell liquid which the cell walls cannot withstand.

Disintegration of the biomass by high shear mixing involves the application of high shear forces to the biomass. These high shear forces can be obtained by stirring or other mechanical agitation. Certain fermentors may for example be equipped with stirring devices which are capable of providing the required high shear forces in order to disintegrate the biomass. During fermentation stirring will be adapted to the optical growth or natamycin production conditions for the biomass. After fermentation stirring will be adapted in order to disintegrate the biomass for example by applying high stirring velocities. High shear mixing may also for example be accomplished by using high shear Waring (or other) blenders.

Disintegration of the biomass by treatment with surface active agents may involve for example the use of octylphenoxypolyethoxyethanol compounds, such as Triton type compounds. The fermentation broth may be incubated with for example 0.01 to 1% for example Triton X-100 during for example 1 to 24 hours.

After the biomass disintegration-step, the natamycin is separated from the biomass. Due to the disintegration treatment, the biomass now mainly consists of small solid particles and/or solubilized matter. Where conventional separation techniques used in the recovery processes for fermentation products are mainly used to separate the solid from the liquid phase, the separation techniques used in the present invention preferably separates solid particles from other solid particles, for example on the basis of size differences or density differences. The separation techniques used in the present invention will not result in a clear liquid phase, but will result in a troubled liquid phase that contains most of the smaller or less dense solid particles (mainly comprising the disintegrated biomass).

In order to separate the biomass from the natamycin particles the fermentation broth can, for example, be treated using a gravity gradient separation technique. The gravity gradient separation technique separates the natamycin particles from both soluble and insoluble impurities. Gravity gradient separation techniques include, for example gravity gradient centrifugation, and may, for example, use upflow columns and hydrocyclones. Gravity gradient separation techniques make use of the principle that particles of different densities and/or sizes can be separated when these particles of different densities and/or sizes are subjected to gravity or equivalent forces.

During the biomass disintegration the biomass particles become smaller. This makes it possible to separate the biomass from the natamycin particles. Usually more than 90% of the disintegrated biomass and other impurities can be removed with the gravity gradient separation technique. Separation efficiency can be increased by adding water and/or a salt (e.g. sodium chloride) to the broth.

The use of gravity gradient separation techniques has the advantage that it is possible to easily modify or direct the process according to the desired purity and yield of the final product. By varying the operation conditions, the purity or the yield can be increased. In general when the purity increases, the yield will decrease and vice versa. The process according to the invention can for example provide natamycin of about 70 w/w % (anhydrous basis) on dry matter with a yield of about 90%. Using different process parameters natamycin of about 90 w/w % purity (anhydrous basis) on dry matter with a yield of about 80% can also be obtained with the process of the present invention. It is even possible to produce several products of different qualities from one fermentation broth.

Gravity gradient separation techniques will give better results, e.g. higher purities and/or yields, if the difference in particle density and/or size between the product particles and the impurities is increased. Therefore it is preferred that the fermentation broth contains natamycin particles having an average particle diameter of at least 2 micrometer. Preferably the average natamycin particle diameter is at least 5 micrometer, more preferable at least 10 micrometer. Fermentation broths containing natamycin particles with an average diameter of about 25 micrometer have been observed. Since natamycin may be present in the fermentation broth with diameters ranging from below 0.05 micrometer to about 40 micrometer, it will be clear to one skilled in the art that the smallest particles may be lost during separation. Furthermore, it will be clear to one skilled in the art that fractions of natamycin particles with large diameters of high purity may be obtained using the gravity gradient separation technique. The conditions under which the gravity gradient separation technique is operated determine which fraction of the natamycin will be recovered. In general larger natamycin particles can, for example, be obtained by using low shear conditions during the fermentation, or by seeding the fermentation with small natamycin particles or by prolonging the fermentation.

Gravity gradient centrifugation can be simulated on laboratory scale by operating a batchwise centrifuge for a shorter time or with a lower number of revolutions per minute as compared to the standard operation of the centrifuge, which would result in a clear separation of the solids from the liquids.

On a production scale the centrifuge is usually operated continuously. As compared to the standard operation of this type of centrifuge, the hold up time in the centrifuge is decreased in order to separate the natamycin from the disintegrated biomass. The lower the hold up time, the higher the purity and the lower the yield of the obtained natamycin. One skilled in the art is able to find a suitable hold up time corresponding to an optimized or desired purity:yield ratio.

After the separation step the natamycin suspension may, for example, be dried in order to obtain a dry product. Any convenient drying technique can be used, e.g. vacuum drying, conduction drying or convection drying. Since natamycin is stable in the crystalline form thereof [natamycin.$3H_2O$], it is critical not to dry the product to a moisture content below about 7%. Vacuum drying is preferably conducted at about 40° C.

After the separation step the natamycin suspension may be further purified, if desired, by a second round of a disintegration step, followed by a second separation step. Several rounds of this process may be used to result in natamycin of about 90 w/w % purity (anhydrous basis) on dry matter, with a yield of about 80%.

The present invention will now be further described in the following Examples.

EXAMPLE 1

A fermentation broth of *Streptomyces natalensis* containing natamycin having an average particle diameter of about 10 micrometer was incubated at a temperature of 30° C. for 3 hours. This thermally treated broth was further treated to a gravity gradient centrifugation. An Alfa-Laval type Feux standard nozzle centrifuge was operated under such conditions that part of the biomass solids was removed together with the supernatant. This treatment resulted in a natamycin suspension of 70 w/w % natamycin (anhydrous basis) on dry matter. The natamycin yield was about 97%.

EXAMPLE 2

To 20 liters of end-product of Example 1, which contained 3.2 kg natamycin, sodium hydroxide was added to adjust the pH to 9.5 to disintegrate the remainder of the impurities. 10 liters of water was added to the alkaline suspension to lower the viscosity and to increase the efficiency of the following gravity gradient centrifugation step.

The diluted, alkaline suspension was centrifuged twice by gravity gradient centrifugation to remove the remainder of the impurities and to concentrate the natamycin suspension. For the gravity gradient centrifugation a Beckmann type J-6M/E centrifuge, using a rotor-type JS 5.2, was operated at 3,500 rpm for 3 minutes. After centrifugation the supernatant was removed and the natamycin containing debris was resuspended in water.

The pH of the purified natamycin suspension was adjusted to 7 by adding hydrochloric acid to the suspension. The suspension was dried.

A dry active product was obtained which had a purity of 92 w/w % natamycin (anhydrous basis) on dry matter.

The total recovery yield of the combined processes of Examples 1 and 2 was about 85%.

EXAMPLE 3

The pH of a fermentation broth of *Streptomyces natalensis* containing of natamycin particles was adjusted to 9.5 by addition of 25 wt % NaOH-solution and incubated for two hours at a temperature of 30° C.

The thus treated fermentation was centrifuged by gravity gradient centrifugation using a Beckmann centrifuge (type J-6M/E; using a rotor type JS 5.2) for 3 minutes at 3500 rpm.

The supernatant was discarded and the pellet containing natamycin particles was resuspended in water of pH 9.5. After resuspension the suspension was centrifuged as before.

After the second centrifugation the supernatant was removed and the pH of the pellet containing natamycin particles was adjusted to 7.0 by addition of 25 wt % HCl solution.

The pellet was dried for 10 hours under vacuum at a temperature of 40° C. A dry active product was obtained containing 90 wt % natamycin (on anhydrous basis).

EXAMPLE 4

A fermentation broth of *Streptomyces natalensis* containing natamycin particles was diluted with water.

The diluted fermentation broth was divided in two parts:

Part A was incubated for two hours at 30° C. at a pH of 9.5, resulting in disintegrated biomass. The thus obtained broth was divided in two parts (A1 and A2).

Part B was directly divided in two parts (B1 and B2).

From part A and Part B the first parts (A1 and B1) were centrifuged at 5000 rpm for 10 minutes and the second parts (A2 and B2) were centrifuged at 3500 rpm for 5 minutes.

After centrifugation the natamycin yield and the natamycin contents of the pellets were determined. The results are shown in Table 1. Centrifugation was performed using a Beckmann type J-6M/E centrifuge and a rotor type JS5.2.

TABLE 1

| | Centrifuge conditions | | | |
| --- | --- | --- | --- | --- |
| | bowl speed (rpm) | time (min) | % natamycin yield | % natamycin on dry matter |
| A1 | 5000 | 10 | 96 | 43 |
| A2 | 3500 | 5 | 93 | 68 |
| B1 | 5000 | 10 | 99 | 29.6 |
| B2 | 3500 | 5 | 97 | 31.0 |

Centrifugation at 5000 rpm for 10 minutes resulted in clear supernatants, whereas centrifugation at 3500 rpm for 5 minutes resulted in turbid supernatants.

Samples A1 and A2 relating to fermentation broths with disintegrated biomass show enhanced natamycin purities compared to samples B1 and B2 relating to the original diluted fermentation broths.

Sample A2, obtained after centrifugation of the disintegrated biomass under gravity gradient centrifugation conditions resulting in solid/solid separation, shows a remarkable increase in natamycin purity.

What is claimed is:

1. A process for the recovery of solid natamycin from an aqueous fermentation broth comprising the steps a) to c) in the following order:

a) culturing a natamycin producing microorganism in an aqueous fermentation broth to produce at least 2 g/l of solid natamycin in particle form, wherein the aqueous fermentation broth comprises the solid natamycin particles and the biomass of the cultured microorganism;

b) treating the aqueous fermentation broth containing at least 2 g/l of solid natamycin to disintegrate the biomass therein into biomass particles smaller than the natamycin particles or having a lower density than the natamycin particles, wherein the difference in size or density between the disintegrated particles and the natamycin particles is sufficient to separate the natamycin and biomass particles from each other by a gravity gradient separation technique while maintaining aqueous conditions, and then c) separating solid natamycin from both the aqueous fermentation broth and the disintegrated biomass by using a gravity gradient separation technique to obtain an aqueous natamycin suspension, and recovering solid natamycin therefrom.

2. The process according to claim 1 wherein the fermentation broth comprises at least 7 g/l natamycin.

3. The process according to claim 1 wherein the fermentation broth comprises natamycin particles having an average particle diameter of at least 2 microns.

4. The process according to claim 3 wherein the natamycin particles have an average particle diameter of at least 5 microns.

5. The process according to claim 3 wherein the natamycin particles have an average particle diameter of at least 10 microns.

\* \* \* \* \*